United States Patent
Ellman

(10) Patent No.: US 9,775,665 B2
(45) Date of Patent: Oct. 3, 2017

(54) FIXED POSITION RF ELECTRODE

(71) Applicant: Alan G Ellman, Hewlett, NY (US)

(72) Inventor: Alan G Ellman, Hewlett, NY (US)

(*) Notice: Subject to any disclaimer, the term of this patent is extended or adjusted under 35 U.S.C. 154(b) by 485 days.

(21) Appl. No.: 14/207,485

(22) Filed: Mar. 12, 2014

(65) Prior Publication Data
US 2014/0276757 A1 Sep. 18, 2014

Related U.S. Application Data

(60) Provisional application No. 61/801,266, filed on Mar. 15, 2013.

(51) Int. Cl.
*A61B 18/14* (2006.01)
*A61B 18/00* (2006.01)
*A61B 18/12* (2006.01)

(52) U.S. Cl.
CPC ........ *A61B 18/1402* (2013.01); *A61B 18/149* (2013.01); *A61B 2018/00083* (2013.01); *A61B 2018/00166* (2013.01); *A61B 2018/00589* (2013.01); *A61B 2018/00601* (2013.01); *A61B 2018/00642* (2013.01); *A61B 2018/00708* (2013.01); *A61B 2018/00744* (2013.01); *A61B 2018/00779* (2013.01); *A61B 2018/00791* (2013.01); *A61B 2018/00827* (2013.01); *A61B 2018/00875* (2013.01); *A61B 2018/00886* (2013.01); *A61B 2018/00892* (2013.01); *A61B 2018/00904* (2013.01); *A61B 2018/126* (2013.01); *A61B 2018/1286* (2013.01); *A61B 2018/1407* (2013.01); *A61B 2018/1417* (2013.01); *A61B 2018/1472* (2013.01); *A61B 2018/1495* (2013.01); *A61B 2218/002* (2013.01); *A61B 2218/003* (2013.01); *A61B 2218/007* (2013.01)

(58) Field of Classification Search
CPC .............. A61B 18/1402; A61B 18/148; A61B 18/1485; A61B 2018/1472; A61B 2018/1495; A61B 2018/00607
USPC ........................................ 606/37, 41, 48, 50
See application file for complete search history.

(56) References Cited

U.S. PATENT DOCUMENTS

| | | | |
|---|---|---|---|
| 5,171,240 A * | 12/1992 | Hanwong | A61F 2/18 606/1 |
| 5,562,503 A | 10/1996 | Ellman | |
| 5,954,686 A | 9/1999 | Garito | |
| 6,585,732 B2 | 7/2003 | Mulier | |
| 6,652,514 B2 | 11/2003 | Ellman | |
| 6,764,487 B2 | 7/2004 | Mulier | |

(Continued)

FOREIGN PATENT DOCUMENTS

KR 2011-156383 8/2011

OTHER PUBLICATIONS

International Search Report and written opinion for PCT/US 2014/026887 filed Mar. 13, 2014.

*Primary Examiner* — Thomas Giuliani

(57) ABSTRACT

In one aspect, a fixed position RF electrode for conducting surgical procedures, includes a main device body detachably connectable to an RF generating system, a first polarized conductor and a second oppositely polarized conductor, a bipolar electrical conduit passing through the main device body that passes RF energy from the RF generating system to the first polarized conductor and the second oppositely polarized conductor, and a bipolar electrode for contacting a surgically operative material.

16 Claims, 14 Drawing Sheets

(56) References Cited

U.S. PATENT DOCUMENTS

| | | |
|---|---|---|
| 6,827,715 B2 | 12/2004 | Francischelli |
| 7,094,231 B1 | 8/2006 | Ellman |
| 7,247,155 B2 | 7/2007 | Hoey |
| 7,364,578 B2 | 4/2008 | Francischelli |
| 7,364,579 B2 | 4/2008 | Mulier |
| 7,674,261 B2 | 3/2010 | Garito |
| 7,811,282 B2 | 10/2010 | McClurken |
| 7,967,816 B2 | 6/2011 | Ocel |
| 8,216,233 B2 | 7/2012 | McClurken |
| 8,348,946 B2 | 1/2013 | McClurken |
| 8,361,068 B2 | 1/2013 | McClurken |
| 8,475,455 B2 | 7/2013 | McClurken |
| 2005/0033278 A1* | 2/2005 | McClurken ............ A61B 18/14 606/41 |
| 2005/0245923 A1* | 11/2005 | Christopherson .. A61B 18/1477 606/41 |
| 2008/0097429 A1 | 4/2008 | McClurken |
| 2009/0254077 A1 | 10/2009 | Craig |
| 2009/0264879 A1* | 10/2009 | McClurken ............ A61B 17/32 606/33 |
| 2012/0330307 A1 | 12/2012 | Ladtkow |

\* cited by examiner

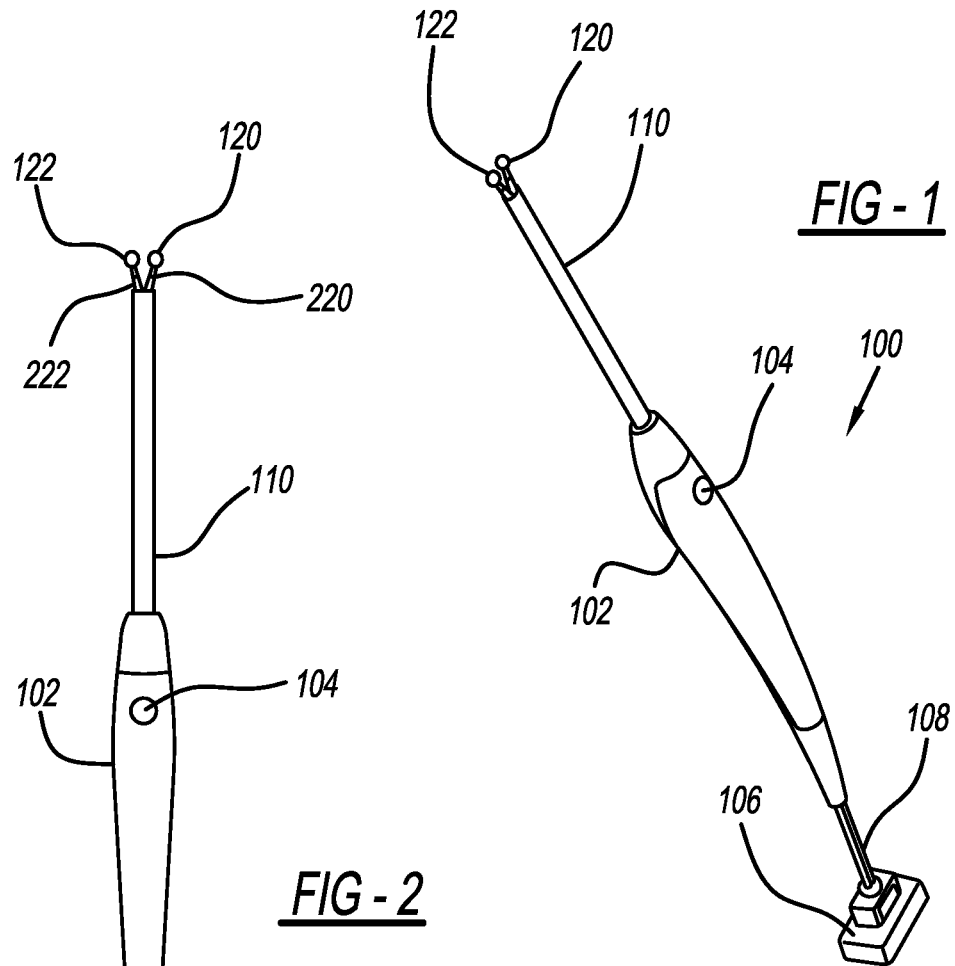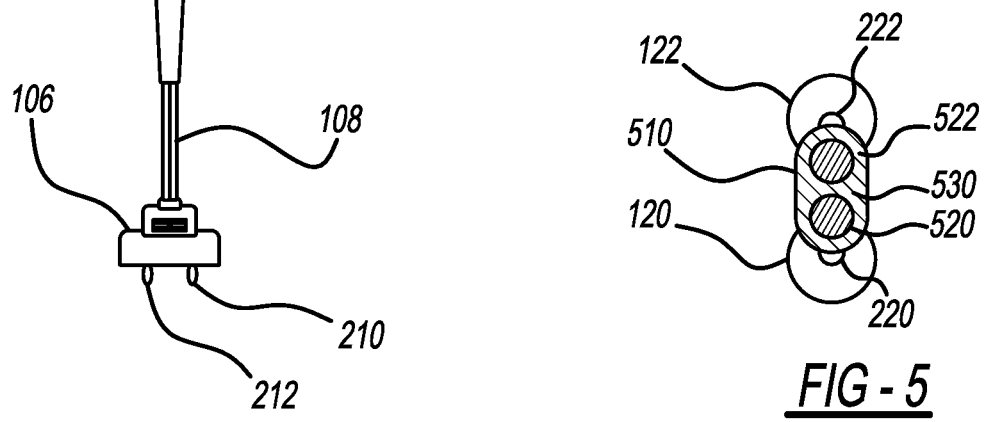

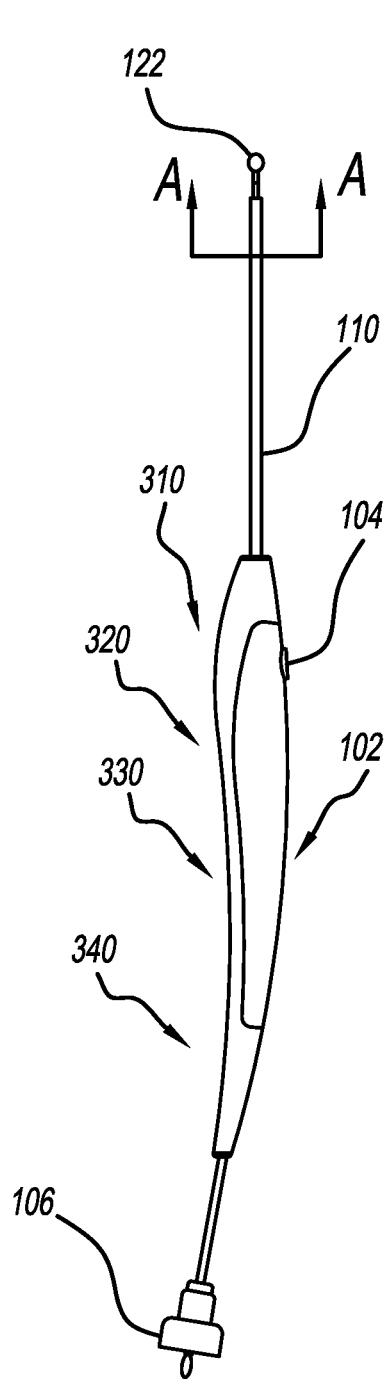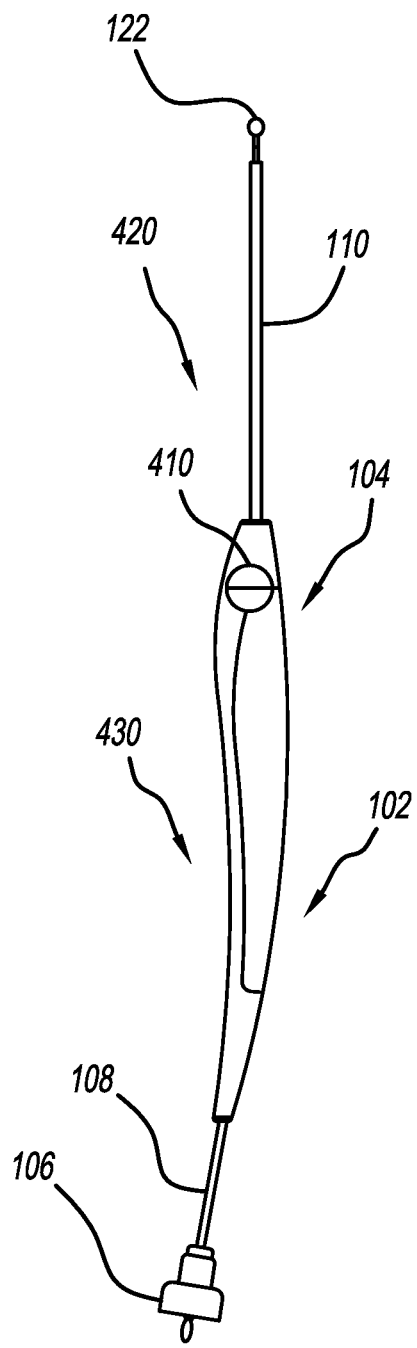
FIG - 3
FIG - 4

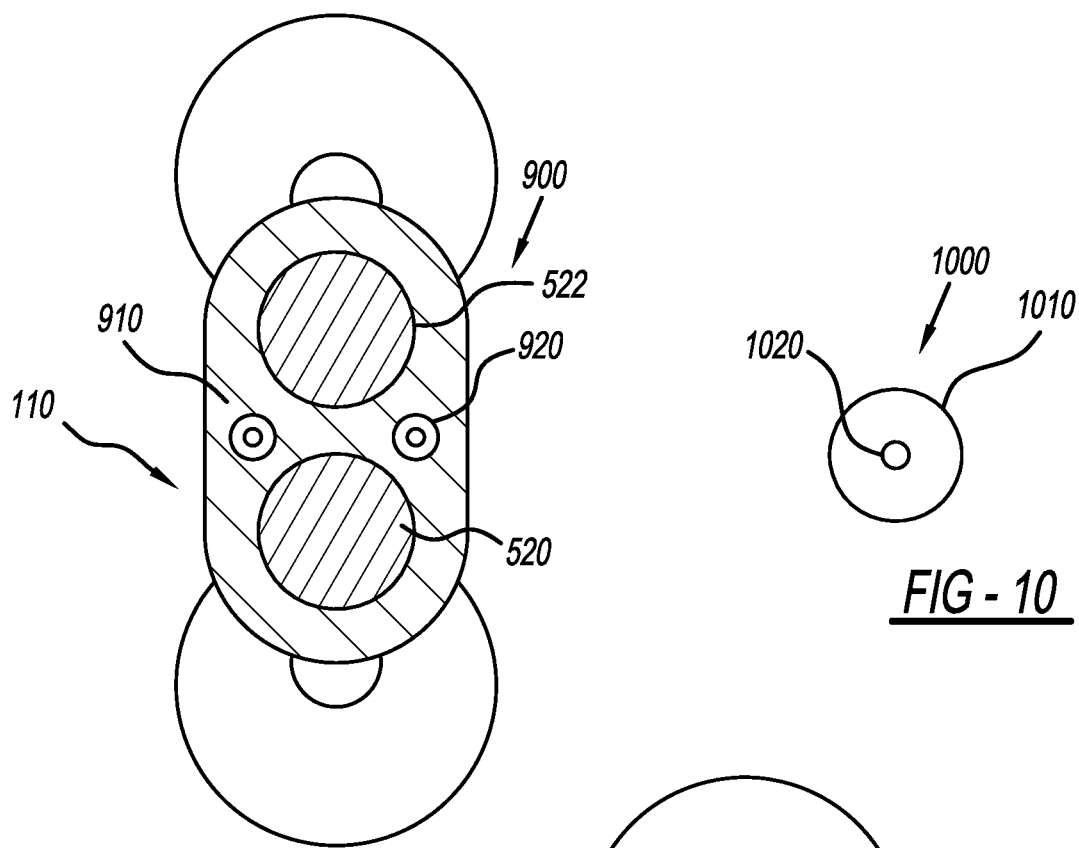
FIG - 9
FIG - 10
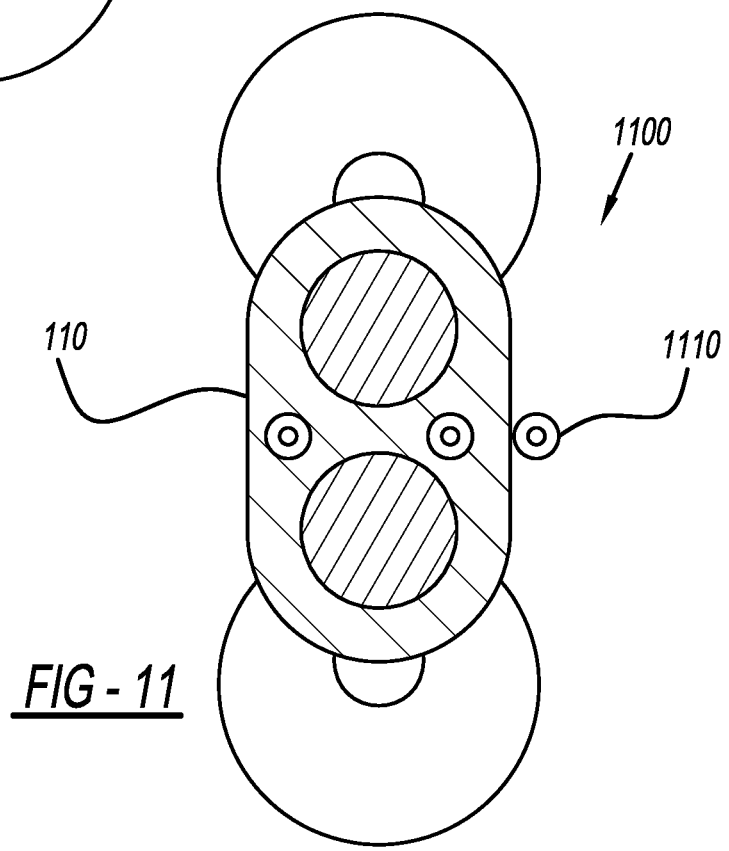
FIG - 11

FIXED POSITION RF ELECTRODE

CROSS REFERENCE TO RELATED APPLICATIONS

The present application is a Utility Application basing priority to provisional application No. 61/801,266 for a Radiowave System, the entirety of which is hereby incorporated by reference.

BACKGROUND

Electrosurgical instruments are well known and widely used in the medical, dental, and veterinarian fields. Electrosurgical instruments utilizing RF energy require adjustment of different operational parameters to achieve the desired surgical results for procedures such as cutting tissue and coagulating blood vessels. It would be useful to provide an instrument that achieves enhanced surgical accuracy, ease of use, and increased utilization of RF energy to perform surgical procedures while minimizing some of the negative effects of these instruments such as the pressing or pulling forces on tissue causing tears or electrosurgical arcing which can cause tissue burns. An electrosurgical tool adapted to respond to operational parameters such as power settings, temperature control, moisture levels, electrode configurations and RF energy settings would be useful in the surgical field.

SUMMARY OF THE INVENTION

In one aspect, a fixed position RF electrode for conducting surgical procedures, includes a main device body detachably connectable to an RF generating system, a first polarized conductor and a second oppositely polarized conductor, a bipolar electrical conduit passing through the main device body that passes RF energy from the RF generating system to the first polarized conductor and the second oppositely polarized conductor, and a bipolar electrode for contacting a surgically operative material. The bipolar electrode includes a first electrode portion positioned at a tip of the bipolar electrode and in electrical communication with the first polarized conductor, a second electrode portion positioned at the tip of the bipolar electrode in electrical communication with the second polarized conductor; and an isolating region formed in between first electrode portion and the second electrode portion preventing electrical current flow between said first electrode portion and said second electrode portion. A first delivery conduit attached to the main device body and adapted to direct a liquid to a region of the surgically operative material in electrical contact with the first electrode portion. A second liquid delivery conduit attached to the main device body and adapted to direct a second liquid to a region of the surgically operative material in contact with the second electrode portion.

BRIEF DESCRIPTION OF THE DRAWINGS

FIG. 1 is a perspective view of a fixed position RF electrode according to an aspect of the invention;

FIG. 2 is a top view of a fixed position RF electrode according to an aspect of the invention;

FIG. 3 is a left side view of a fixed position RF electrode;

FIG. 4 is a left side view of a fixed position RF electrode;

FIG. 5 is a cross-section view cut along A-A of a fixed position RF electrode of FIG. 3 according to an aspect of the invention;

FIG. 9 is a cross-sectional view cut along A-A of FIG. 3 illustrating a delivery system for a fixed position RF electrode;

FIG. 10 is a cross-sectional view of a delivery system tube for a fixed position RF electrode according to an aspect of the invention;

FIG. 11 is a cross-sectional view cut along A-A of FIG. 3 illustrating an external delivery system for a fixed position RF electrode;

DETAILED DESCRIPTION OF PREFERRED EMBODIMENTS

Figure 6:
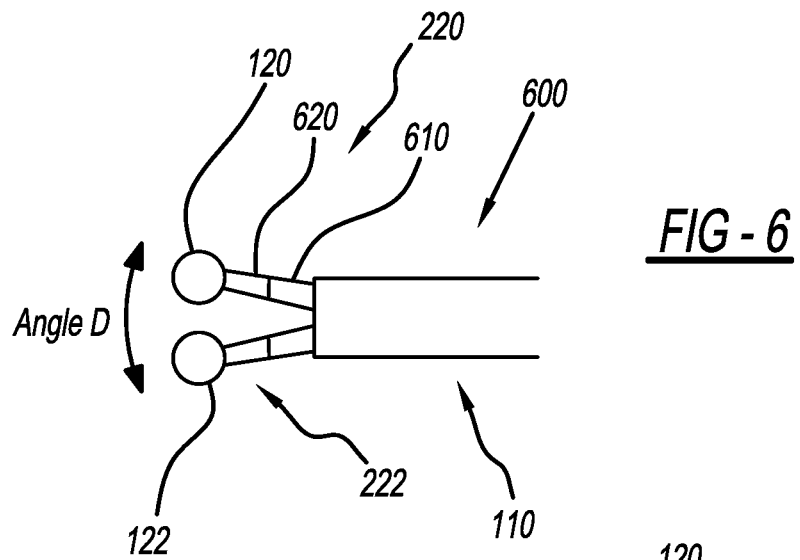
FIG. 6 is a top plan view of the distal end of a fixed position RF electrode.

FIG. 1 is a perspective view of a fixed position RF electrode 100. The fixed position RF electrode 100 includes a body 102, an energizer button 104, a plug 106, a cord 108, an extension 110, a first electrode 120, and a second electrode 122. Body 102 provides a gripping area for a surgeon to hold fixed position RF electrode 100. Body 102 also provides structure for electrical components that may be included therein. Cord 108 connects plug 106 to body 102. Plug 106 is intended to be received by a RF generating apparatus. U.S. Pat. No. 7,674,261 is incorporated by reference herein and provides an example of an RF generating device.

Extension 110 extends distally and terminates with first electrode 120 and second electrode 122. Fixed position RF electrode 100 (e.g., an electrosurgical system) may be used, for example, to provide tissue hemo stasis as well as cutting and coagulation, fulguration, ablation, desiccation, vaporization, among other uses.

FIG. 2 is a top plan view of a fixed position RF electrode. A first pole 210 and a second pole 212 extend from plug 106 and are electrically conductive. When plugged into a RF generating apparatus, first pole 210 and second pole 212 provide energy through cord 108 into body 102. Switch 104 allows control by a surgeon to turn on and off the RF energy. When switched on, RF energy flows through extension 110 to a first electrode lead 220 and a second electrode lead 222. First electrode lead 220 is attached to first electrode 120 and second electrode lead 222 is attached to second electrode 122. Thus, when a surgeon turns on an RF energy source by depressing switch 104, energy may flow from first pole 210 through cord 108, body 102, switch 104, first electrode lead 220 and first electrode 120. The RF energy may then pass through the patient, patient fluids, adjuvant fluids, irrigation fluids, and complete the circuit by flowing into second electrode 122, second electrode lead 222, cord 108, and second pole 212.

First electrode 120 and second electrode 122 may be spherical (e.g., ball-shaped) and may generally be in the range of 3-5 mm (three to five millimeters) in diameter. However, as discussed herein the geometry and dimensions of first electrode 120 and second electrode 122 may be modified and are not limited to the as-shown geometries.

FIG. 3 is a left side view of a fixed position RF electrode. Body 102 may have other areas of interest including a front portion 310, a front finger portion 320, a central portion 330, and a rear finger portion 340. When a surgeon grips body 102, their index finger may be in the region of front finger portion 320. Their hand may be generally placed around central portion 330, with the pinky being located near rear finger portion 340. Front portion 310 may or may not be gripped by the surgeon's hand. A cross-section shown A-A of extension 110 is shown in more detail in FIG. 5.

FIG. 4 is a left side view of a fixed position RF electrode. A center of gravity 410 is shown to provide the region where fixed position RF electrode 100 is generally balanced. A distal portion 420 is in front of center of gravity 410. A proximal portion 430 is shown rearward of center of gravity 410. Proximal portion 430 may also include generally the weight of cord 108 and plug 106. However, proximal portion 430 may not include the weight of cord 108 and/or plug 106 if their mass is sufficiently small or negligible.

By providing a center of gravity where most of the mass is near the surgeon's hand (e.g., see central portion 330), it provides a nimble use of fixed position RF electrode 100. One skilled in the art will recognize other variants on this center of gravity configuration and the present invention is not limited to that described herein. Moreover, where the fixed position RF electrode 100 includes sensitive settings (e.g., for voltage, frequency, and/or current), then having a late distal portion 420 may allow the surgeon to use fixed position RF electrode 100 without the mass of fixed position RF electrode 100 pressing on tissue or fluids. This may allow a more efficient use of fixed position RF electrode 100 where the mass of fixed position RF electrode 100 is not interfering with the surgical procedure. In general, some fixed position RF electrodes 100 performance improves the lighter the application of pressure of the electrodes 120, 122. Thus, the balance of fixed position RF electrode 100 may provide for more delicate usage, and improved performance. Where the balance of fixed position RF electrode 100 in the user's hand provides for a light touch, the mass is provided in the hand region so that there is less mass toward the distal end, providing a light and gentle application to tissue and fluids.

FIG. 5 is a cross-sectional view A-A of the fixed position RF electrode of FIG. 3. First electrode 120 and second electrode 122 are shown connected to the extension cross-section 510 of extension 110 by first electrode lead 220 and a second electrode lead 222, respectively. Extension cross-section 510 foot is shown generally encapsulating a first electrode wire 520 and a second electrode wire 522. Separation insulation 530 may be made of a material that insulates the RF energy flowing through extension 110.

Figure 14:
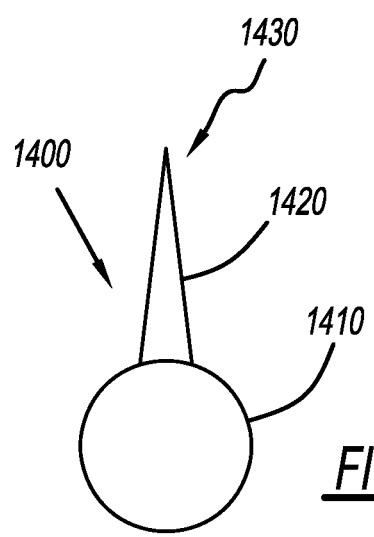
FIG. 14 illustrates a top view of an electrode with additional features according to an aspect of the invention.
Figure 15:
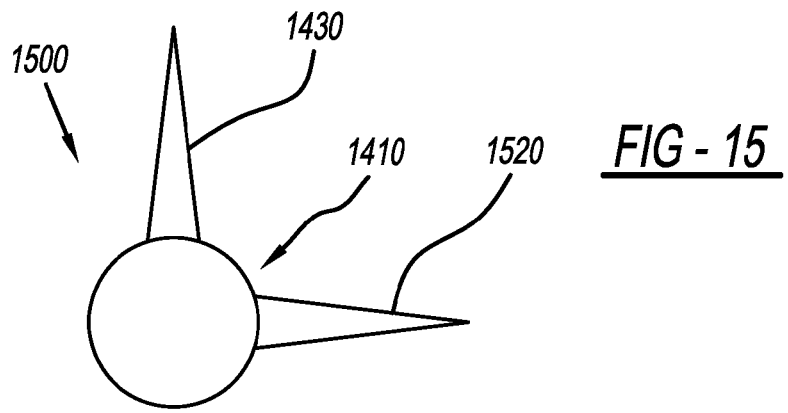
FIG. 15 illustrates a top view of an electrode with additional features according to an aspect of the invention.
Figure 16:
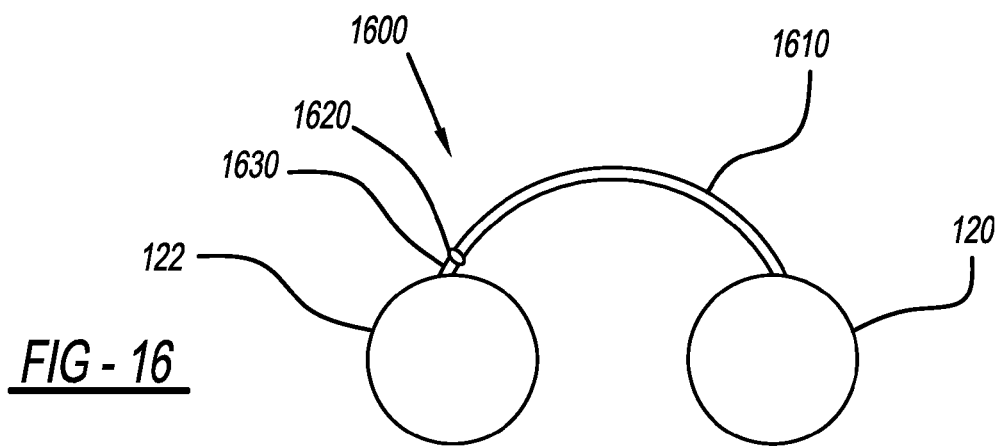
FIG. 16 illustrates a top view of an electrode with additional features according to an aspect of the invention.

FIG. 6 is a top plan view of the distal end 600 of a fixed position RF electrode. First electrode 120 and second electrode 122 are shown as separated by an angle D. The angle D may be provided as a fixed angle (e.g., where first electrode lead 220 and second electrode lead 222 are rigid), or angle D may be adjustable by the operator (e.g., the surgeon), where first electrode lead 220 and second electrode lead 222 are flexible. The angle provided may be, for example 50°. This angle D may also be adjusted based on the shape of first electrode 120 and second electrode 122. The shape of first electrode 120 and second electrode 122 may be spherical, as shown, or they may include other geometries such as elliptical, conical, pure metal, flat, or they may include protrusions as shown in FIGS. 14-16.

As shown, second electrode lead 222 diverges (e.g., slanted out at an angle) from first electrode lead 220 by angle D. As such, the width and/or diameter of extension 110 is reduced and provides enhanced visibility to the operator. As such the visibility of first electrode 120 and second electrode 122 are improved, as well as the visibility of the surgical site.

First electrode lead 220 includes a first electrode section 610 and a second electrode section 620. The second electrode section 620 and first electrode section 610 may be made from different materials. For example, the wire within extension 110 may be rigid or semi-rigid. However, the portion of second electrode section 620 may be flexible allowing the operator to adjust (e.g., bend) the second electrode section 620 so that first electrode 120 and second electrode 122 may be modified.

Figure 7:
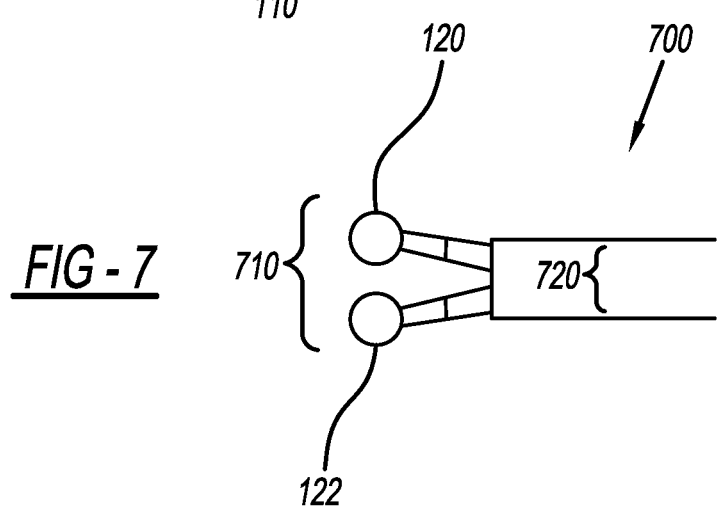
FIG. 7 is a top plan view of the distal end of a fixed position RF electrode.

FIG. 7 is a top plan view of the distal end 700 of a fixed position RF electrode. A first width 710 shows the outer width of the electrodes 120, 122. Insofar that a second width 720 is narrower than first width 710, improved vision is provided for the operator at the surgical site, and at the electrodes 120, 122 themselves.

Figure 8:
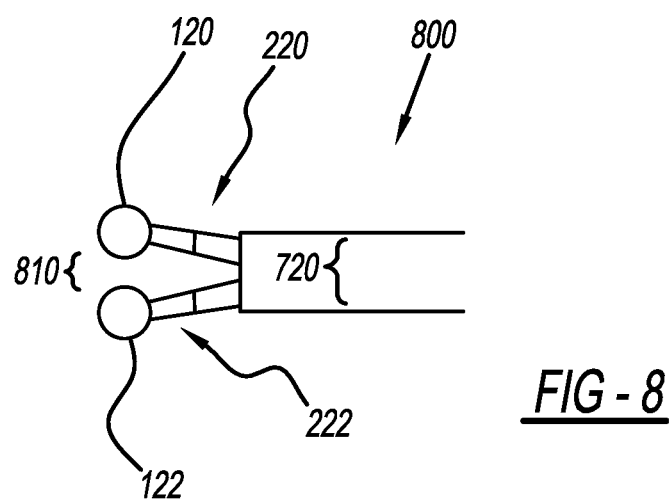
FIG. 8 is a top plan view of the distal end of a fixed position RF electrode.

FIG. 8 is a top plan view of the distal end 800 of a fixed position RF electrode. A gap width 810 shows the distance between the inside surfaces of first electrode 120 and second electrode 122. In a fixed electrode system, gap width 810 may be fixed as well, although they may be configured with divergent first electrode lead 220 and second electrode lead 222.

FIG. 9 is a cross-sectional view of a delivery system 900 for a fixed position RF electrode. The cross-section of extension 110, as shown herein, may include a first delivery system 910 and a second delivery system 920. They may coexist within extension 110 with first electrode wire 520 and second electrode wire 522. In general, first delivery system 910 and second delivery system 920 may be tubes that selectively transport irrigation, antibiotic, anticoagulant, and/or pain medication. However, first delivery system 910 and second delivery system 920 are not limited to these types of liquids to be delivered to the surgical site.

FIG. 10 is a cross-sectional view of a delivery system tube 1000 for a fixed position RF electrode. A delivery system body 1010 (e.g., a tube) may include a micro perforation 1020 for misting. Thus, the types of liquids carried by a delivery system (e.g., first delivery system 910 and second delivery system 920) may be selectively misted at the surgical site. Moreover, first delivery system 910 may include a misting system and second delivery system 920 may not include a misting system. However, either may be used. This would allow for example where some liquids allow for misting while others may not.

The diameter and geometry of micro perforation 1020 may be determined based on the material being delivered, the pressures provided, and/or the flow rate desired. Moreover, the angle at the micro perforation 1020 may provide a narrow mist or a wide spray of mist. Examples of diameters for micro perforation 1020 may include 0.012 mm (point zero one two millimeters) to 0.2 mm (point two millimeters) provided from 10 PSI (ten pounds per square inch) to 500 PSI (five hundred pounds per square inch).

Continuing in reference to FIGS. 9 and 10, delivery systems 910 and 920 may be adapted to deliver a liquid, such as saline, to body tissue at a surgical site and in operation with electrodes 120 and 122, or other electrode arrangements, to increase the effectiveness of an electrosurgical procedure as will be discussed below.

FIG. 11 is a cross-sectional view of an external delivery system 1100 for a fixed position RF electrode. An external delivery system 1110 may be included outside of extension 110. This may be a tube selectively attached to extension 110, or it may be molded into or personally attached to extension 110. Where external delivery system 1110 is selectively attached, the surgeon may decide what type of delivery system to attach to fixed position RF electrode 100 while performing a procedure. For example, if a high rate of flow for irrigation is desired, a larger inner diameter tube may be selectively attached. Alternatively, where a low rate of flow is desired, a smaller inner diameter two may be attached. In another example, misting may be desired and a tube having a misting end (e.g., as described in FIG. 10) may be attached.

Figure 12:
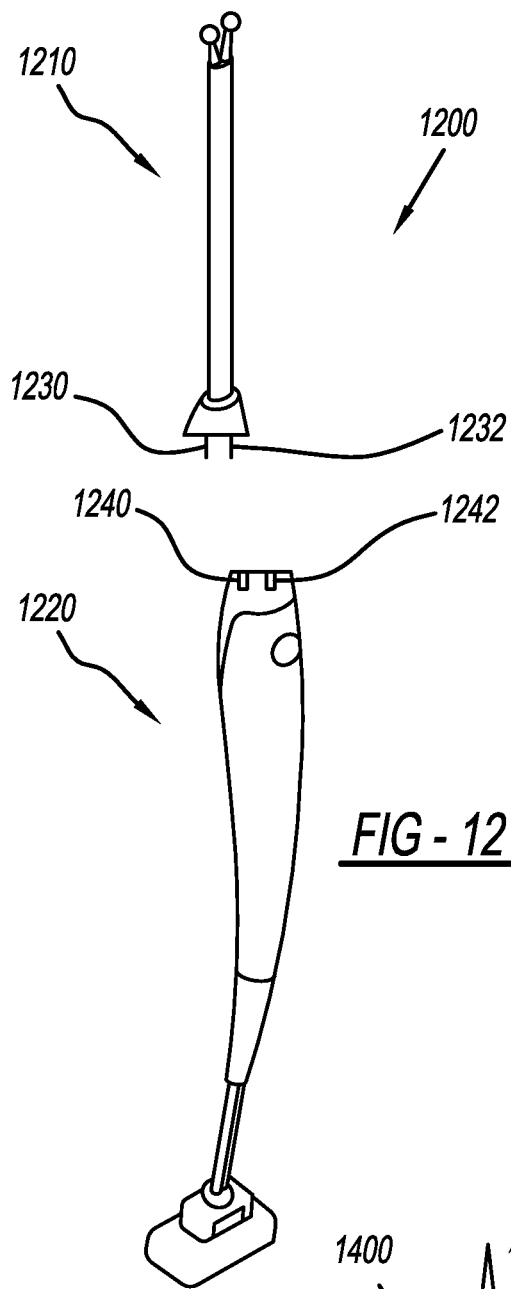
FIG. 12 is a left perspective view of a fixed position RF electrode according to an aspect of the invention.

FIG. 12 is a left perspective view of a separable fixed position RF electrode 1200 with the electrode system detached. A detachable electrode 1210 may be provided with a first electrode lead 1230 and a second electrode lead 1232. The separable handpiece 1220 may include a first receiving socket 1240 and a second receiving socket 1242. This may allow for different detachable electrodes 1210 to be selected during a procedure. This mail also allow for reuse of separable handpiece 1220. While it is shown that detachable electrodes 1210 include male first electrode lead 1230 and second electrode lead 1232, the male/female orientation of separable handpiece 1220 and detachable electrode 1210 may be reversed.

Figure 13:
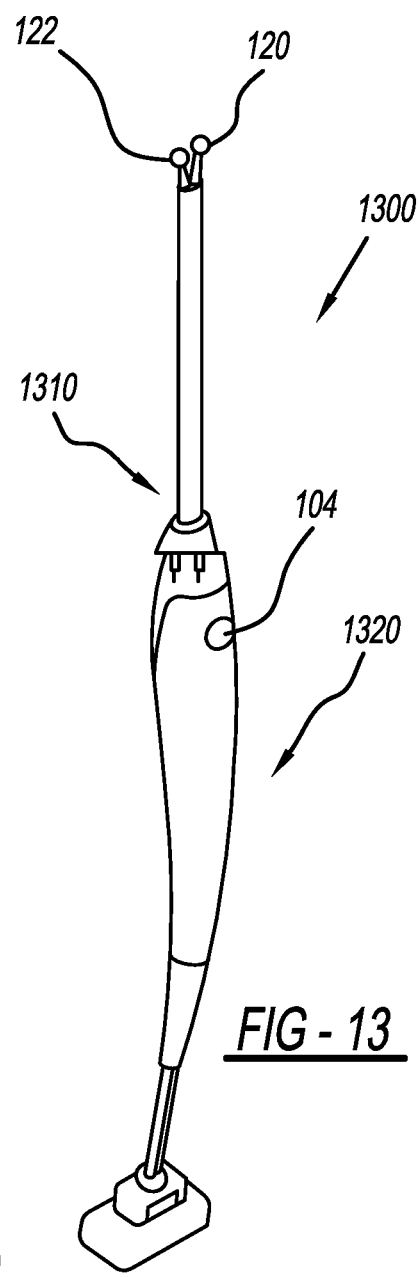
FIG. 13 is a left perspective view of a fixed position RF electrode according to an aspect of the invention.

FIG. 13 is a left perspective view of a separable fixed position RF electrode 1300 with the electrode system attached. Here, detachable electrode 1310 and separable handpiece 1220 are locked in place to form a single unit 1320. When button 104 is activated, energy will flow to first electrode 120 and second electrode 122.

FIG. 14 is an example of an electrode with additional features 1400. Electrode 1410 may be used for either of first electrode 120 and second electrode 122, or both. A body portion 1420 of electrode 1410 may extend the electrode to an end feature 1430. As shown, end feature 1430 is a point. This may allow for a focused application of RF energy when electrode 1410 is energized. In an example, second electrode 122 (see FIG. 1) may be placed to touch patient tissue or fluids and the end feature 1430 (e.g., of first electrode 120) may be touched to the patient for focused application of RF energy. Alternatively, the electrode 1410 may be used in mono-polar or bi-polar mode.

FIG. 15 is an example of an electrode with additional features 1500. Electrode 1410 may include one or more features. As shown, electrode 1410 includes two features including end feature 1430 and a second feature 1520. Each may be selectively applied to the patient for the desired effect. Where electrode 1410 is used for second electrode 122, second feature 1520 points toward first electrode 120 and can be used in bi-polar mode to perform the procedure. Alternatively, end feature 1430 may be used in mono-polar mode.

FIG. 16 is an example of two electrodes with additional features 1600. A cutting loop 1610 extends from first electrode 120 toward second electrode 122. An insulating gap 1620 holds cutting loop 1610 stably and attaches cutting loop to second electrode 122, while maintaining electrical separation. Insulating gap 1620 may be made of plastic or another radiofrequency insulating material. An extension 1630 may or may not be present extending from second electrode 122. In this configuration, the surgeon may, for example, use cutting loop 1610 to excise tissue.

Figure 17:
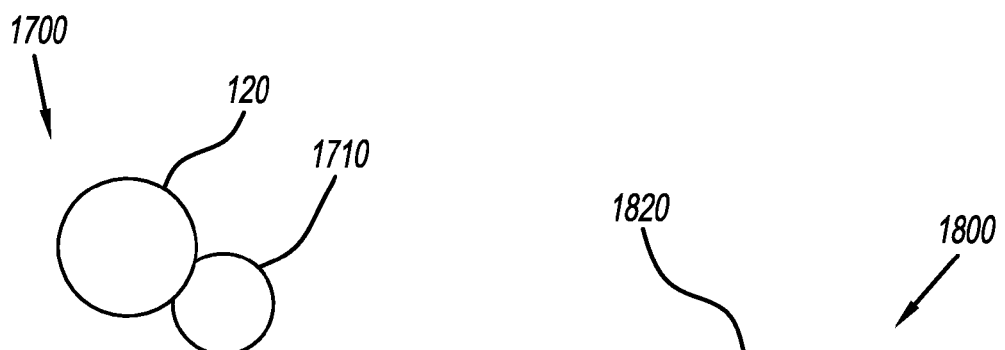
FIG. 17 is top view of an embodiment of an electrode irrigation arrangement according to an embodiment of the invention.

FIG. 17 is an example of an electrode irrigation arrangement 1700. First electrode 120 may include irrigation port 1710 adjacent thereto, or directed to it. This would allow the surgeon to place irrigation at the electrode location, rather than the general surgical site.

Figure 18:
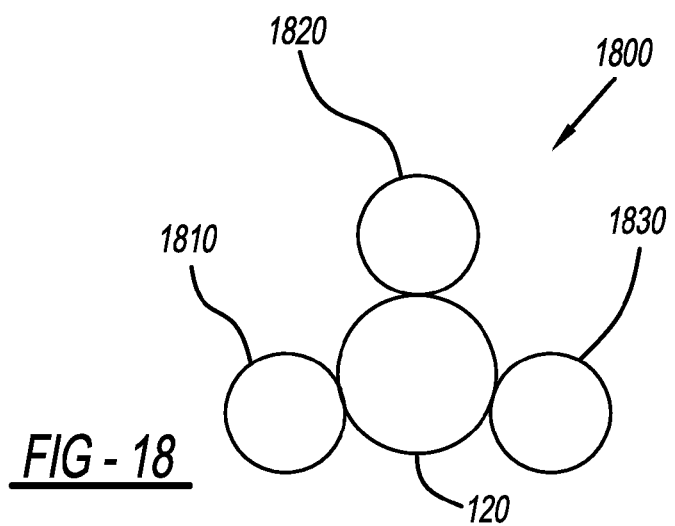
FIG. 18 is top view of an embodiment of an electrode irrigation arrangement according to an embodiment of the invention.

FIG. 18 is an example of an alternative irrigation arrangement 1800. A first irrigation port 1810, a second irrigation port 1820, and a third irrigation port 1830. Each of the irrigation ports 1810, 1820, 1830 may be provided with various fluids for use at the surgical site. For example, first irrigation port 1810 may provide saline, a second irrigation port 1820 may provide antibiotic, and third irrigation port 1830 may provide pain medication.

Figure 19:
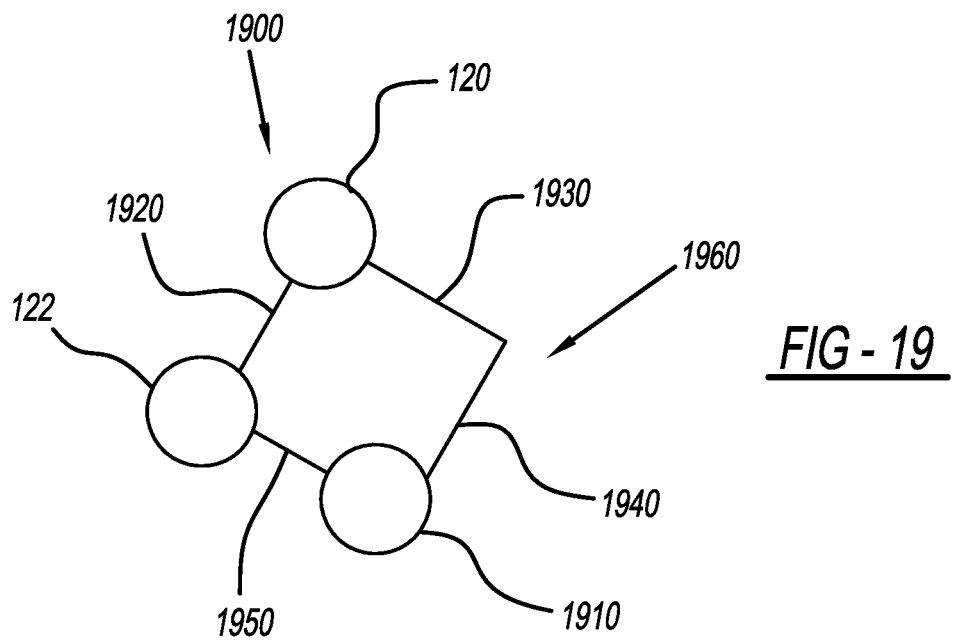
FIG. 19 is top view of an embodiment of an electrode arrangement with additional features according to an embodiment of the invention.

FIG. 19 is an example of an alternative electrode arrangement 1900. First electrode 120 and second electrode 122 may provide for bipolar RF electro-surgery. An insulated structure 1910 may also provide for a wireframe support along with first electrode 120 and second electrode 122. First wireframe component 1920 may be electrically and structurally attached to first electrode 120, and may be structurally attached but insulated from second electrode 122. A second wireframe component 1930 may be electrically and structurally attached to first electrode 120 and structurally attached to insulated structure 1910, along with third component 1940. Fourth wireframe component 1950 may be insulated and structurally attached to second electrode 122 and electrically and structurally connected to first electrode 120 (through wireframe component 1940 and wireframe component 1930). Thus, wireframe component portions 1920, 1930, 1940, 1950 may be formed from a single wire or may be formed from separate pieces. Using the diamond region 1960, the operator may cut provided the pattern of the wire (as shown a "V" shape). Alternatively, the operator may turn the fixed position RF electrode 100 and use first electrode 120 and second electrode 122 normally.

Figure 20:
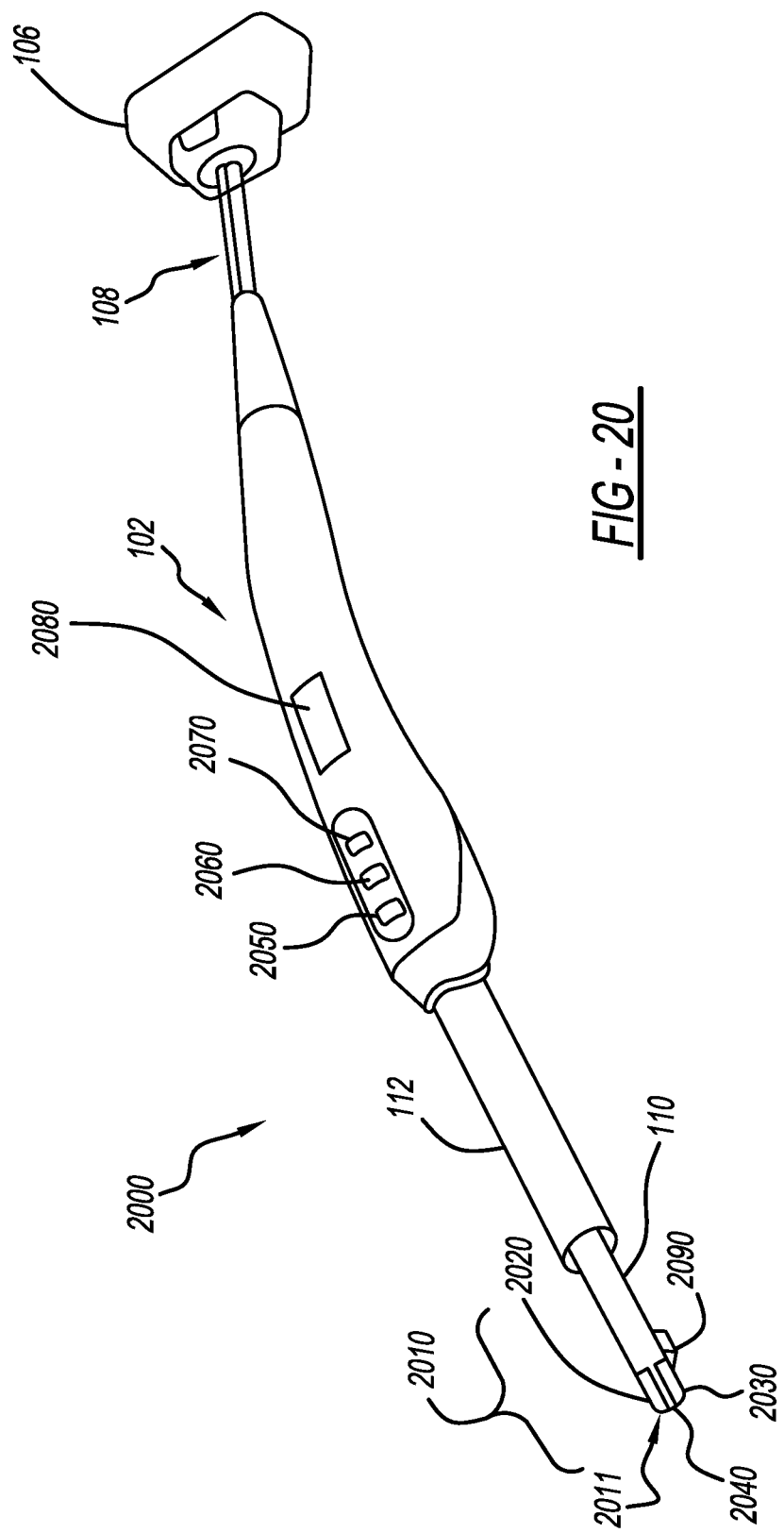
FIG. 20 is a perspective view of a fixed position RF electrode according to an embodiment of the invention.

FIG. 20 shows an embodiment of a fixed position RF electrode 2000. The fixed position RF electrode 2000 includes a bipolar electrode 2010 located within sheath 112 and including an electrode tip 2011. In this example bipolar electrode 2010 is a single electrode design comprised of two differently polarized electrode portions 2020 and 2030 formed together in a single shaft with an isolating region 2040 between the two. Charged electrode portion 2020 is isolated electrically from oppositely charged electrode portion 2030 by isolating region 2040 which may be formed of a material such as a plastic polymer insulator. The two electrode portions 2030 and 2020, as one shaft in a single electrode design, may be formed from materials that permit flexibility of the bipolar electrode 2010. When used in a surgical procedure, the two electrode portions 2020 and 2030 formed as one piece provide for precise and accurate positioning of the bipolar electrode 2010 for surgical procedures with minimal gap between the electrode portions. The bipolar electrode 2010 may be configured as a detachable electrode or formed as a single unit with fixed position RF electrode 2000. Each electrode portion 2020 and 2030 is connected individually and electrically though extension 110 to cord 108 to plug 106 and to a RF generating apparatus. A first pole 210 and a second pole 212 extend from plug 106 and are electrically conductive. When plugged into a RF generating apparatus, first pole 210 and second pole 212 provide energy through cord 108 into body 102. Switch 104 allows control by a surgeon to turn on and off the RF energy. When switched on, RF energy flows through extension 110 to electrode portion 2020 and to electrode portion 2030. Thus, when a surgeon turns on RF energy by depressing switch 104, energy may flow from first pole 210 through cord 108, body 102, a first conductor in extension 110 to electrode portion 2020. The RF energy may then pass through the patient, patient fluids, adjuvant fluids, irrigation fluids, and complete the circuit by flowing into second electrode portion 2030 to a second conductor in 110 to connect to cord 108, and second pole 212.

Continuing with FIG. 20, the fixed position RF electrode 2000, in one embodiment, includes buttons, 2050, 2060, and 2070, on the top surface of body 102 and which may be pressed to initiate a features of the fixed position RF electrode 2000 as will be discussed in further detail below. Other examples of the invention may include a different number of buttons.

The fixed position RF electrode 2000 includes a sensor 2090 located near the electrode tip 2011. Sensor 2090 may be attached to the electrode 2010 in close proximity to electrode tip 2011, or sensor 2090 may be integrated into the electrode 2010 and formed into a portion of the isolating material 2040, or sensor 2090 may be attached separately to sheath 112. In one embodiment, sensor 2090 monitors different parameters related to the operating characteristics of the fixed position RF electrode 2000. The parameters monitored by the sensor may include a number of parameters including, but not limited to, temperature, voltage, current flow rate, the hydration or calcification of body tissue from a surgical site, moisture levels, or any other parameters related to the operation of the fixed position RF electrode 2000. The sensor 2090 may be one or more of a type of sensor including a moisture sensor, optical sensor, electrical or magnetic field sensor, electrical circuit, capacitance proximity sensor, or others. It should be understood by those skilled in the art that various types of sensors may be employed to monitor the fixed position RF electrode 2000 operational parameters.

In an embodiment of fixed position RF electrode 2000, sensor 2090 communicates electrically with controller 2080 to provide measurements, data, and signals from the operational parameters of fixed position RF electrode 2000 to the controller 2080 which may be used by the controller 2080 to adjust operational settings of the fixed position RF electrode 2000. One embodiment of a system for communication between sensor 2090 and controller 2080 includes electrical wires connected to sensor 2090 and adapted for connection to controller 2080 through the interior of sheath 112 into the body 102 of the fixed position RF electrode to controller 2080. In another embodiment, sensor may be attached to extension 110 and wiring may be formed into and insulated within extension 110 to controller 2080. Communication between sensor 2090 and controller 2080 may wireless or Bluetooth communication.

FIG. 20 illustrates controller 2080 as located in the body 102 of fixed position RF electrode 2000. However controller 2080 may be located separately from the fixed position RF electrode 2000 such as a part of a remote RF generating system or a computer, but still in connection to communicate electronically with features of the fixed position RF electrode 2000. Controller 2080 is in electrical connection with cord 108 and plug 106 and to receive power.

Figure 21:
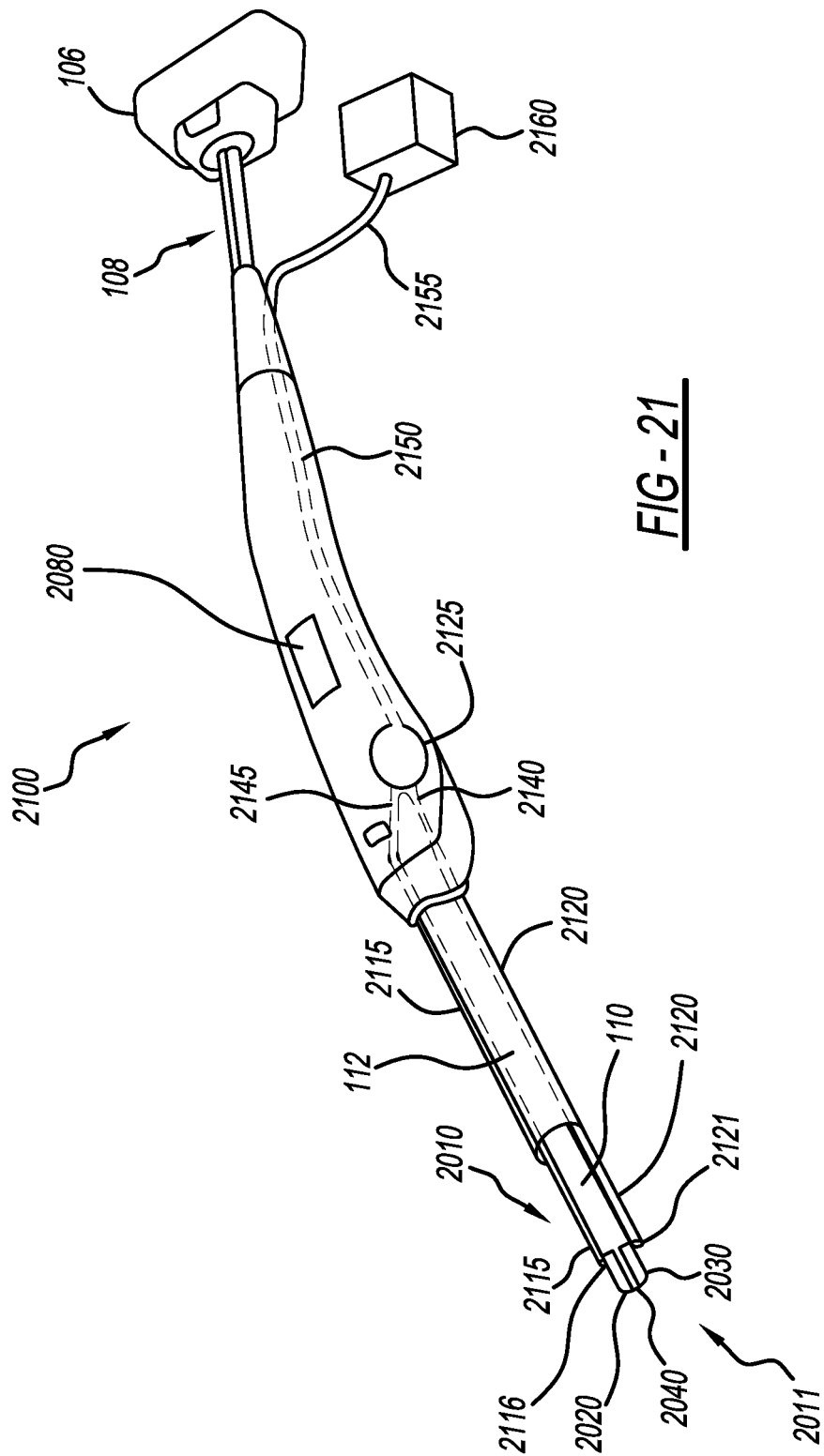
FIG. 21 is a perspective view of a fixed position RF electrode adapted with a delivery system according to an embodiment of the invention.

FIG. 21 shows a perspective view of an embodiment of a fixed position RF electrode 2100 with bipolar electrode 2010 adjacent delivery tubes 2115 and 2120 which are adapted for delivery of a liquid, spray, or mist to the surgical site in the area of the bipolar electrode tip 2011. In one embodiment, the delivery tubes 2115 and 2120 are situated along side electrode 2010 and coexisting within sheath 112. Tube openings 2021 and 2116 are positioned adjacent tip of electrode 2011 which would typically be situated at point of operation in the surgery site, in order to deliver a liquid spray or mist to the site of surgery. It should be understood that delivery tubes 2115 and 1120 may be of the type illustrated in delivery system 920 and be formed within extension 110.

Continuing with FIG. 21, pump 2125 connects to a liquid source 2160 which may include a bag, IV collapsible bag, or other liquid container to pull liquid from liquid source 2160, through exterior conduit 2155, through interior conduit 2150 to pump 2125. Pump 2125 then delivers liquid through connection points 2140 and 2145 into delivery tubes 2120 and 2115. The spray, mist or liquid pumped out to tubes 2115 and 2120 to be delivered to the site of surgery. A mechanism to polarize the liquid before it arrives at tube openings 2021 and 2116 may be used to provide polarized liquid to the surgical site. Pump 2125 may be a peristaltic type pump or another liquid pumping mechanism. One embodiment includes a pump 2125 in the body 102 of the fixed position RF electrode 2100, but it should be recognized by those skilled in the art that a pumping mechanism may be situated outside of the fixed position RF electrode, still in connection with the liquid source 2160 and the fixed position RF electrode 2100.

In another embodiment, delivery of fluid to the fixed position RF electrode may include connection gravity-fed holding container such as a collapsible bag of saline which is connected to the fixed position RF electrode though 2155 hose that further connects to conduit 2150 into the body 102 of the fixed position RF electrode. This system of providing liquid to the fixed position RF electrode in a gravity fed system and the container or collapsible bag may be installed on a pole or other mechanism to keep the liquid stored above the level of the surgical site so that the liquid will flow down to the site without other means.

In one embodiment, the liquid is a polarized saline solution which is delivered to the surgical site in the region near tip 2011 of bipolar electrode 2010 and the flow rate of saline is controlled. Controller 2080 communicates with pump 2125 for setting and adjusting the flow rate of the delivery of liquid to delivery tubes 2115 and 2120. In one example, the flow rate is set to a pre-set or a constant rate for all operational setting of fixed position RF electrode 2100. In another embodiment, the flow rate is set and adjusted depending on the type of surgical procedure being performed by the surgeon using the fixed position RF electrode 2100. For example, a higher powered surgical setting may use a high flow rate of liquid while a lower powered setting may use a lower flow rate. In one embodiment, buttons 2050, 2060, and 2070 are used to select a certain mode of surgical mode of operation, such as a cutting operation, the flow rate of liquid through pump 2125 may be pre-set for that mode. Controller 2080, when receiving a signal from one or more of buttons 2050, 2060, 2070 selecting a specific mode of surgical operation, adjusts pump 2125 to pump a liquid at a pre-set flow rate for that mode of operation. Low, medium and high liquid flow rate settings and other levels may be pre-set for each mode of surgical operation by compressing one of buttons 2050, 2060 or 2070 multiple times or by another flow rate selection mechanism such as a foot switch or a slider switch.

In another embodiment, sensor 2090 is used to determine how hydrated or calcified the body tissue is near the electrode tip 2011 to determine if more or less liquid is needed at the surgical site and then adjustment is made to the flow rate. Sensor 2090 may sense hydration as well as other parameters from the surgical site and communicate that data to the controller 2080. The controller 2080 is programmed to adjust and maintain operational settings for the fixed position RF electrode 2100 using the signals from the sensor 2080.

Figure 22:
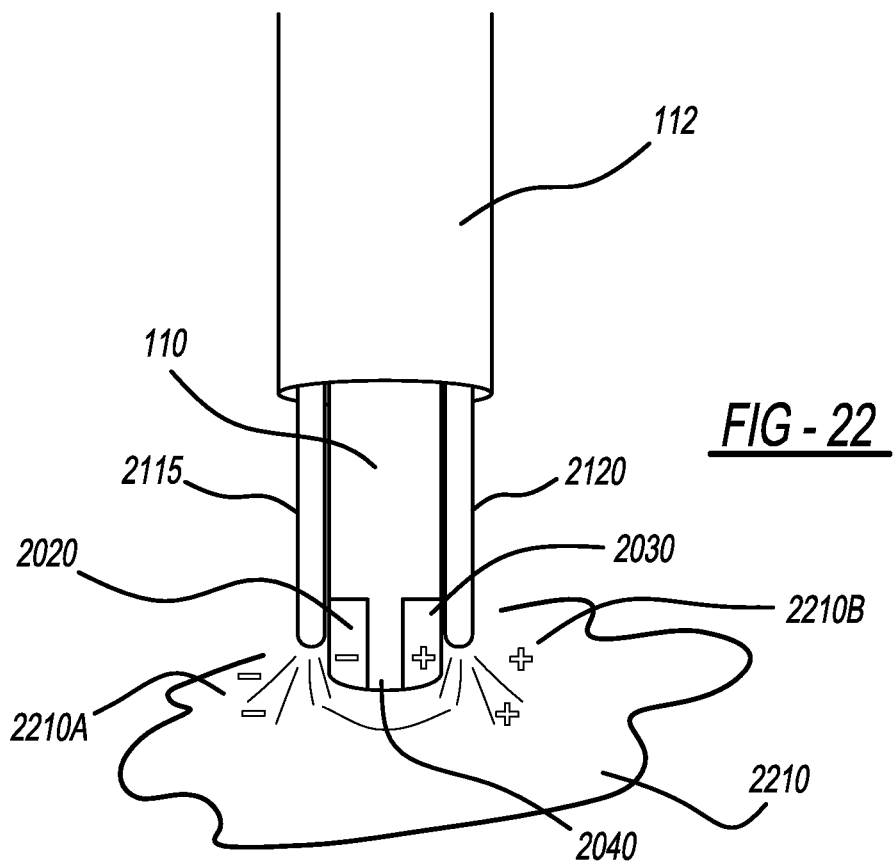
FIG. 22 is a side view a distal end of a fixed position RF electrode adapted with a delivery system according to an embodiment of the invention.

FIG. 22 shows a side view of bipolar electrode 2010 near the electrode tip 2011. A portion of extension 110 is shown with bipolar electrode 2010 including electrode portions 2020 and 2030 extending from it toward a surgical site 2210 which may include a type of body tissue. In this embodiment, electrode portion 2020 is charged as a first polarized setting, for example, negatively charged, while electrode portion 2030 is charged to the opposite polarized setting, for example, positively charged. It is understood that the polarization of the electrode portions 2020 and 2030 could be reversed. Alongside electrode portion 2020 is delivery tube 2115 which extends adjacent extension 110 to deliver a spray, mist, or liquid to the surgical site 2210A near the tip of electrode 2011. In one embodiment, a saline solution may be used and the saline solution is delivered in an ionized state. The saline solution from delivery tube 2115 is electrically charged or polarized to match polarization of electrode portion 2020 and is delivered to surgical site 2210A. In a similar manner, delivery tube 2120 provides ionized liquid or mist such as saline solution to the surgery site 2210B adjacent to electrode portion 2030. In this example, both the saline from delivery tube 2120 and the electrode portion 2030 are positively charged. The liquid in each of delivery tubes 2115 and 2120 is polarized before arrival at the corresponding surgical site.

In one example, the liquid spray or mist delivered in fluid contact with the body tissue of the surgery site 2210 provides an expanded pathway for current to flow between the positively charged electrode portion 2020 to the negatively charged electrode portion 2030. The regions of bipolar saline 2210A and 2210 B create a wider area or pathway for current flow at the surgical site 2210, enhancing the effectiveness of the electrode 2010 for performing surgical procedures, particularly for the surgical procedures involving coagulation.

Figure 23:
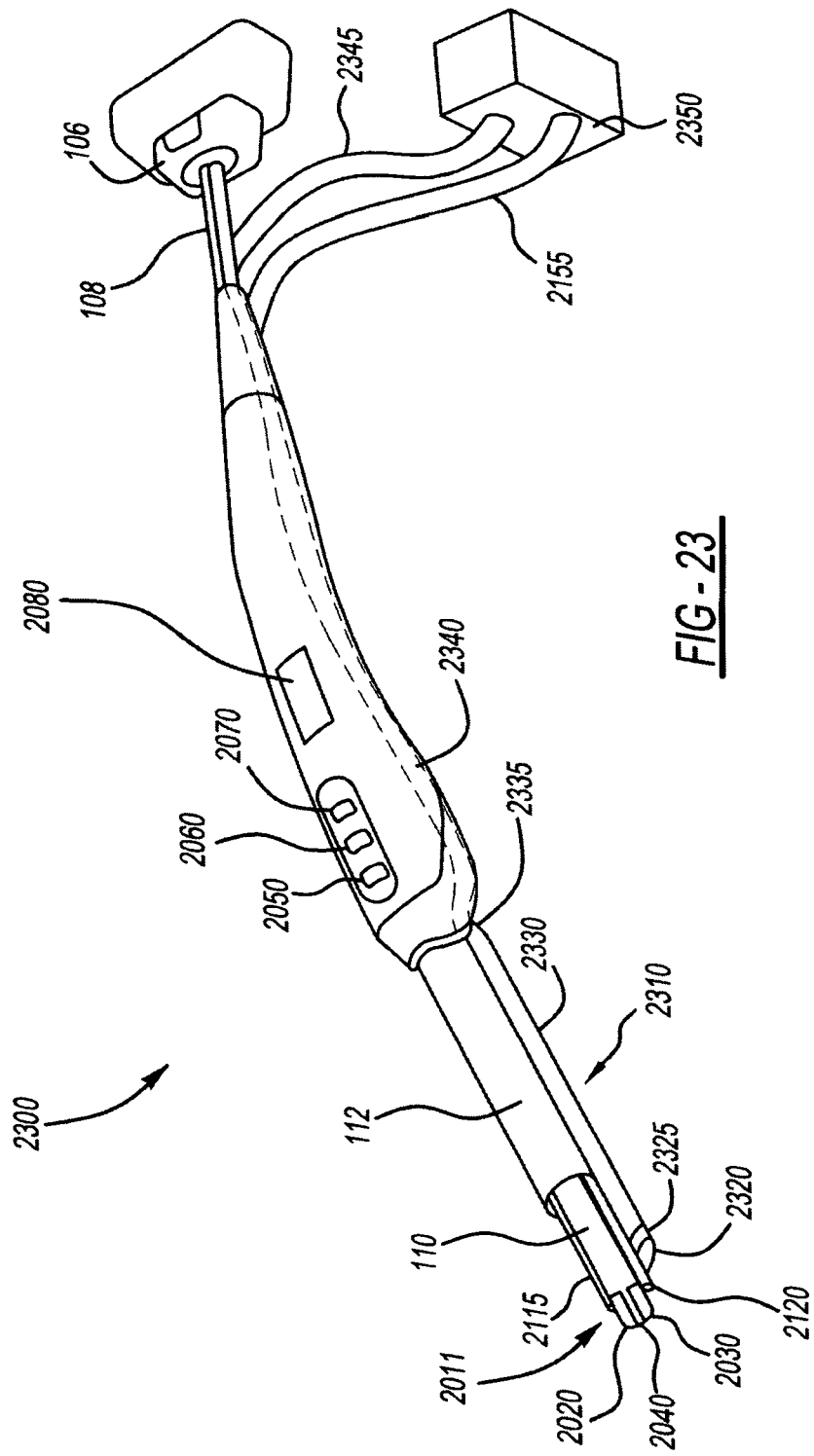
FIG. 23 is a perspective view of a fixed position RF electrode adapted with a collection system according to an embodiment of the invention.

FIG. 23 illustrates a fixed position RF electrode 2300 which includes a fluid uptake system 2310 attached to an outer bottom surface of extension 110 and further connected to an outer bottom surface of sheath 112. It should be understood that fluid uptake system 2310 may be attached in other locations in fixed position RF electrode 2300. Fluid uptake system 2310 includes a flared opening 2320 positioned in close proximity to electrode tip 2011 of electrode 2010 and delivery tubes 2115 and 2120. The flared portion 2320 pulls excess liquid or mist or body fluids from the surgery site and draws them up through tapered portion 2325 and then into uptake tube 2330. Uptake tube 2330 is connected through a portion of body 102 to an interior uptake hose 2340 which then pulls the excess liquids into an uptake hose to a collection system 2350. The collection system 2350 my include a vacuum pump or other mechanism to draw liquids, air, and other matter through the liquid uptake system 2310 and into a collection bag, drain or other disposable collection tray which may be included in the collection system 2350. Fluid uptake system 2310 is activated by any one of different switching systems including a footswitch, button, trigger type switch. Fluid uptake system 2310 is connected to controller 2080 for adjustment of the uptake flow rate of fluids. The flow rate of the fluid through the uptake tube 2330 may be monitored in conjunction with the flow rate of saline delivery to delivery tubes 2115 and 2120 by sensor 2090 and an input sent from the sensor to the controller 2080 which modifies the flow rates in response. In one embodiment, controller 2080 adjusts liquid uptake system 2310 to draw liquid into the uptake tube 2330, to control the areas of polarized liquid such as saline 2210 A and 2210 B, for improved operation of the bipolar electrode 2110 thereby improving the performance of the surgical procedure. Sensor 2090 monitors the surgery site and sends signals to controller 2080 in order to determine adjustments to operational parameters such as saline delivery flow rate, liquid uptake flow rates and other operational settings of the fixed position RF electrode 2300.

Figure 24:
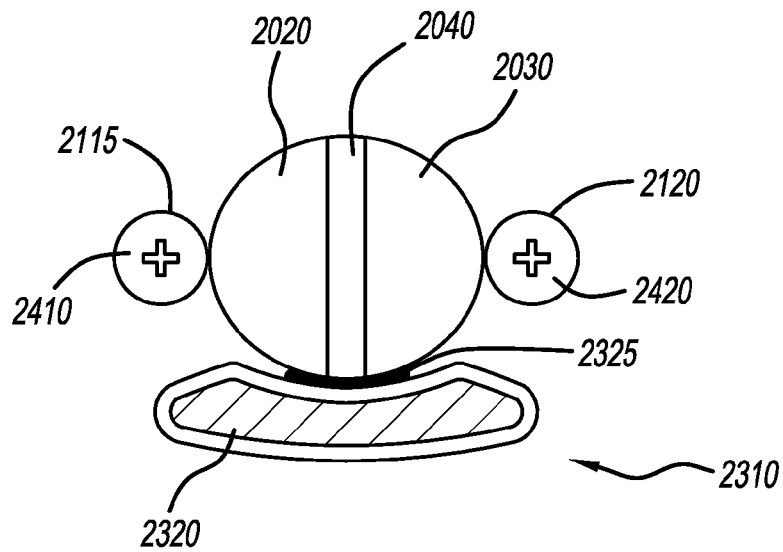
FIG. 24 is a cross-sectional view of fixed position RF electrode of FIG. 23 at a tip of the electrode.

FIG. 24 illustrates a cross section of FIG. 23 at the electrode tip 2011 as viewed from the distal end of the fixed position RF electrode 2300. Electrode portions 2020 and 2030 are shown separated by isolating area 2040 of bipolar electrode 2010. Alongside of electrode 2010 are delivery tubes 2115 and 2120 which include micro perforations 2410 and 2420 through which a liquid such as a conductive saline solution can be delivered. The micro perforations 2410 and 2420 assist in providing a radial shape to the mist or spray of the liquid from delivery tubes 2115 and 2120. In one example, radial spray of mist or liquid enhances the operational characteristics of the device and assists in the prevention of clogging of tubes 2115 and 2120. FIG. 24 illustrates an embodiment of the invention in which a portion of liquid uptake tube 2310 is attached to electrode 2010 at attachment point 2325 and includes a flared opening 2320 to pull liquid from a region adjacent the electrode tip 2011. In one example, the flared opening 2320 includes a region wider than the width of electrode 2010. Liquid uptake tube 2320 could be positioned further away from bipolar electrode 2010 such that a gap of space between the liquid uptake tube and electrode 2010 would be located at the connection point 2325. Liquid uptake tube 2310 may be attached to liquid uptake conduit 2330 which may be made of a flexible material so that conduit 2330 may be bent to position opening 2320 in a particular location or at an particular angle. The shape of flared opening 2320 may be widened or narrowed and may be formed in another shape such as square or oblong to provide optimal capture of liquid materials into uptake conduit 2330.

Figure 25:
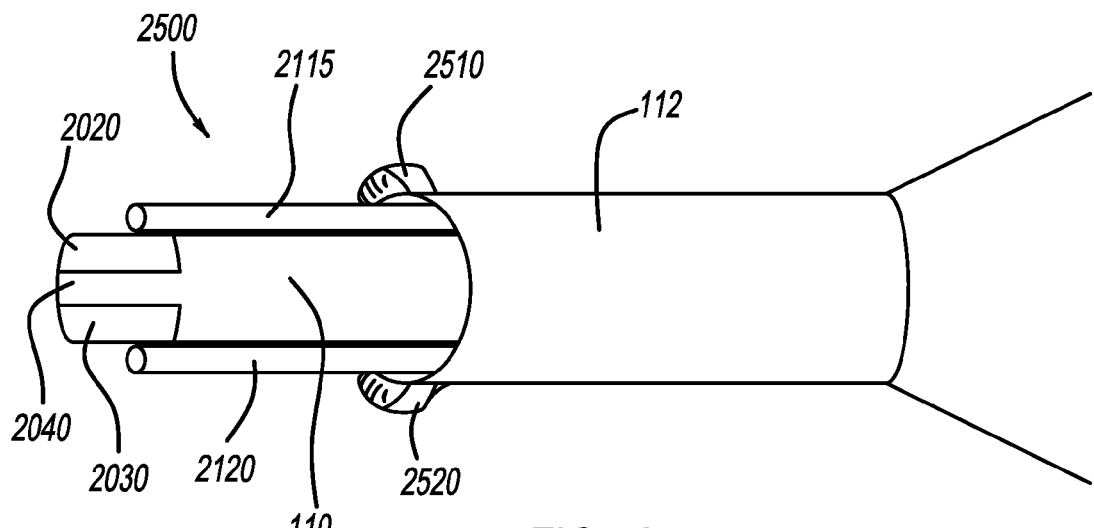
FIG. 25 is a side view a distal end of a fixed position RF electrode adapted with lighting features according to an embodiment of the invention.

FIG. 25 shows a perspective view of one embodiment of fixed position RF electrode 2500 including electrode 2010 with delivery tubes 2115 and 2120 in coexistence with the electrode 2010 inside extension 110 and further including light features 2510 and 2520. In one embodiment, light features 2510 and 2520 are positioned at an end 2530 of sheath 112 so that light projected from light features 2510 an 2510 may be directed to the tip of the electrode 2011 and an area surrounding tip 2011 in the surgery site. The light features 2510 and 2520 may include LED's, fiber optic cables or other lighting mechanisms. The light features may be located closer to electrode tip 2011 or further along sheath 112 toward the body 102 of the fixed position RF electrode 2500 or another part of the fixed position RF electrode 2500 for different direction of the light. In one embodiment, light features 2510 and 2520 may be formed as part of extension 110 or attached to the outside of extension 110 with electrical connection back to buttons 2050, 2060, 2070 for switching of power on and off, and to electrical cord 108 for source of electrical power.

Figure 26:
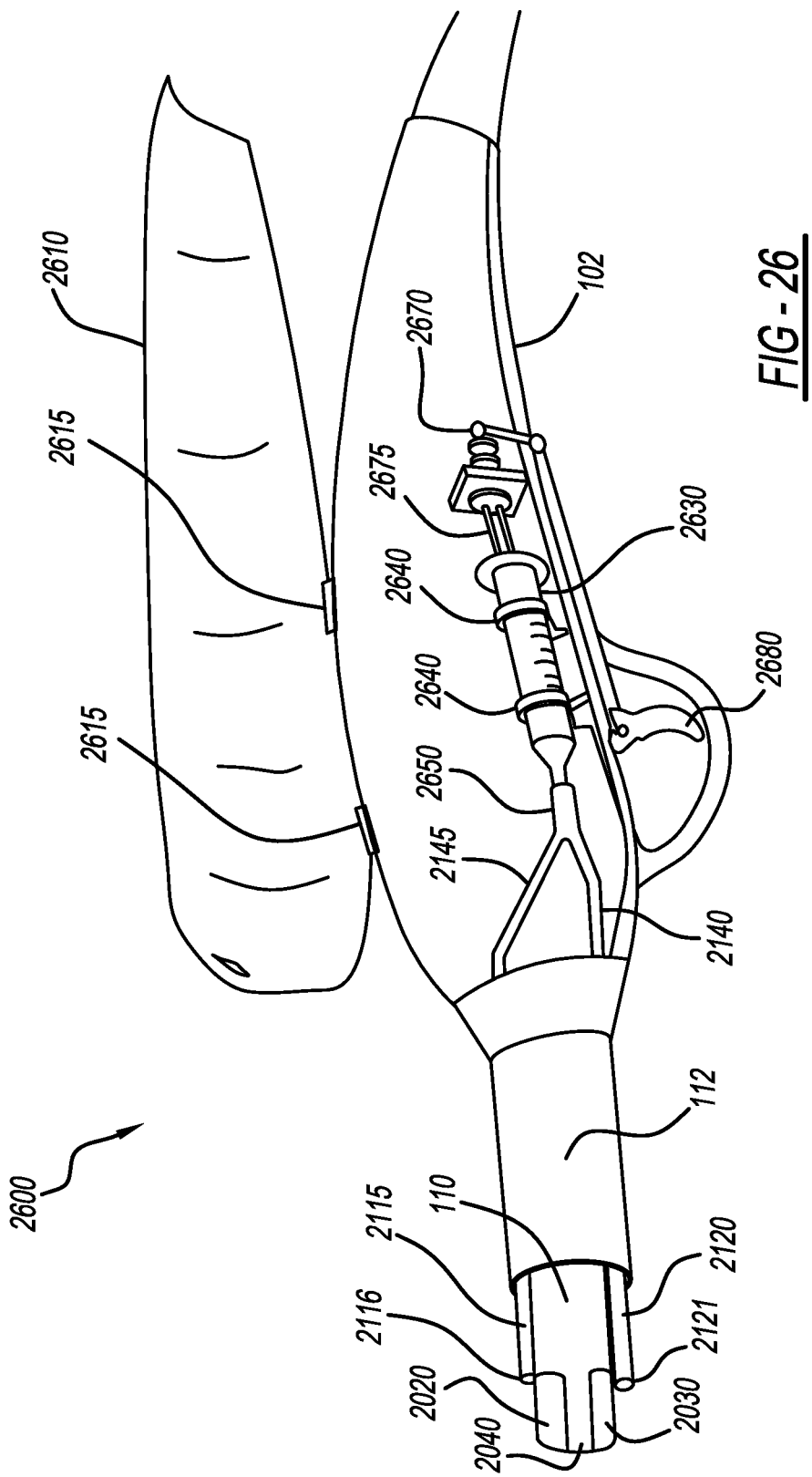
FIG. 26 is a perspective view of a fixed position RF electrode according to an embodiment of the invention.

An embodiment of the invention illustrated in FIG. 23 includes pump 2125, but other methods of liquid delivery may be used. FIG. 26 shows a fixed position RF electrode 2600 which includes a compartmental door 2610 in body 102 of the fixed position RF electrode 2600 which may be opened at hinge points 2615 and includes a compartment 2620 to install a standard syringe 2630 containing liquid for storage and delivery of a liquid to the fixed position RF electrode 2600. Clips 2640 are included in the interior of body 102 to hold syringe 2630 in place. Flexible attachment point 2650 connects an output of the syringe 2360 to conduits 2140 and 2145. Attachment point 2650 may be made of a material such as plastic or rubber to form a water tight connection to a tip of syringe 2360. The interior of body 102 includes lever mechanism 2670 for compressing the plunger 2675 on the syringe 2630 to force the liquid in the syringe 2360 toward attachment point 2650 and into conduits 2140 and 2145 when a user initiates the lever mechanism 2670 or other compression mechanism. The lever mechanism 2670 may be initiated by a footswitch, button 2050 or trigger type mechanism 2680.

Figure 27:
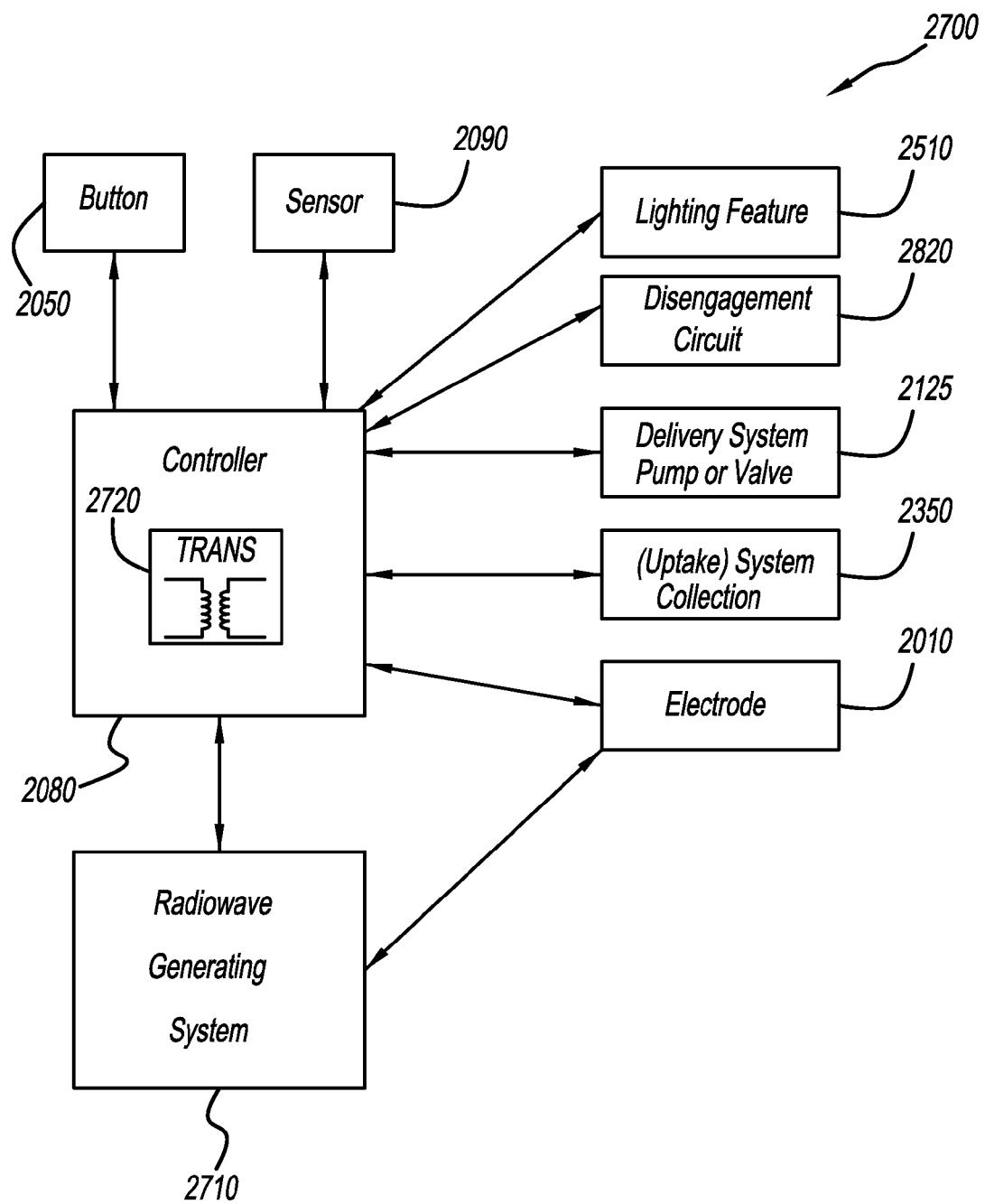
FIG. 27 is a schematic of a fixed position RF electrode according to an embodiment of the invention.

FIG. 27 shows a schematic of the features of an embodiment of fixed position RF electrode 2700. RF generating system 2710 connects to controller 2080. Buttons 2050 (also 2060 and 2070 not shown) connect to controller 2080 providing inputs to controller 2080 for controlling features of the fixed position RF electrode 2700. Sensor 2090 is connected to controller 2080 to provide inputs of operational parameters from the fixed position RF electrode 2700 and from the area of the surgical site 2210 itself. Controller 2080 is connected to bipolar electrode 2010, delivery system pump 2125, fluid collection system 2350, and disengagement circuitry 2820. Each of these features may be in two-way communication with the controller 2080. Controller 2080 may receive input signals from buttons 2050, 2060, 2070, or sensor 2090 or another input such as a switch and, in response, controller 2080 is programmed to adjust one or more operational settings to bipolar electrode 2010, delivery system pump 2125, fluid collection system 2350, and disengagement circuitry 2820, or other features of the fixed position RF electrode 2700 that are connected to the controller 2080. In one embodiment controller 2080 includes transformer circuitry 2720 which may be used to modify electrical characteristics such as power supplied to features of the fixed position RF electrode 2700. For example, transformer circuitry may be used to polarize an electrode portion 2015 or 2020, or to polarize liquid being transported in delivery tubes 2115 and 2120 or to modify electrical power for a delivery system pump 2125 or a lighting feature 2510 and 2520.

Figure 28:
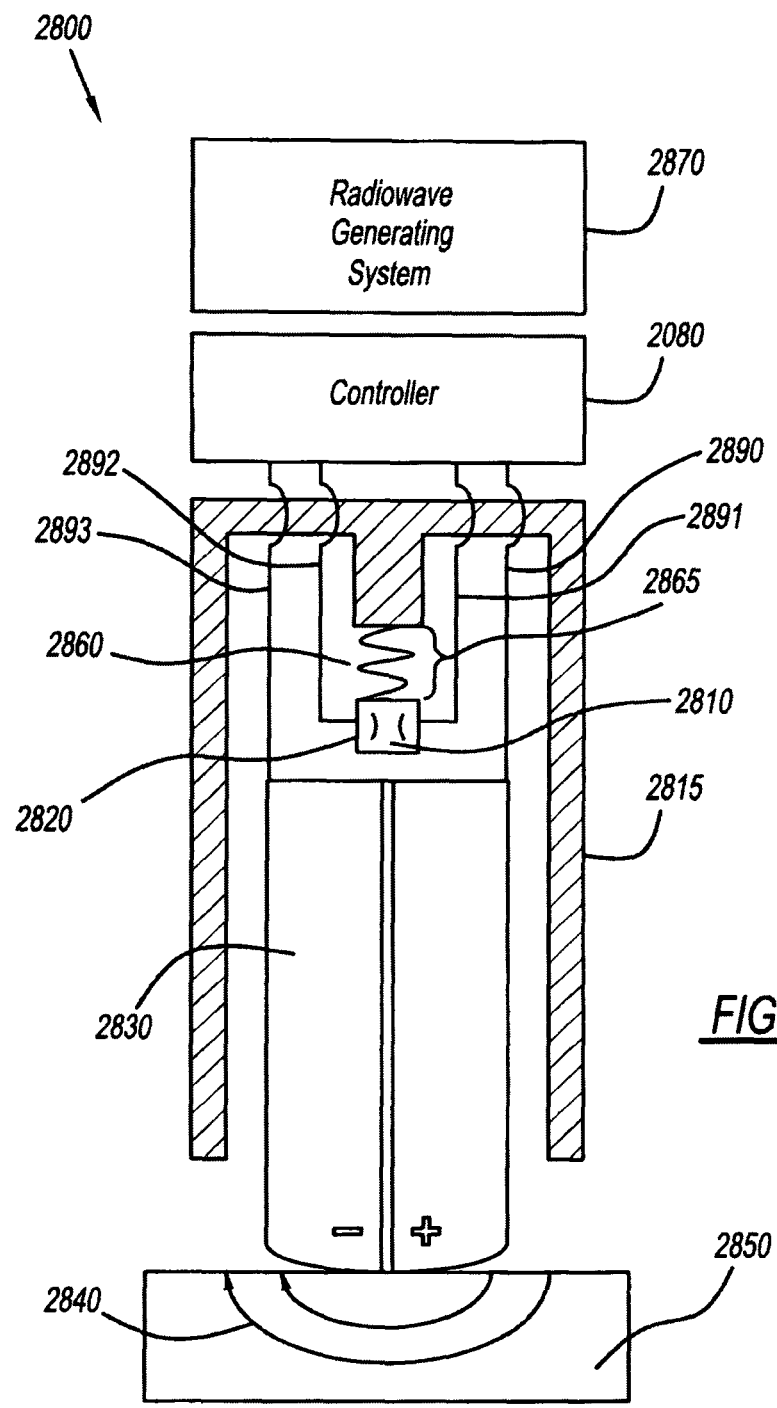
FIG. 28 is a side view of a fixed position RF electrode illustrating a disengagement circuit system according to an embodiment of the invention.

FIG. 28 illustrates an embodiment of fixed position RF electrode 2800 including a disengagement circuitry system 2820. Disengagement circuitry system 2820 includes detection sensor 2810 which is in electrical contact with electrode 2830 and controller 2080. In one example, detection sensor 2810 may be a capacitive touch sensor, a peizo electric sensor, or a mechanical switch adapted to detect when the electrode 2830 disengages from tissue 2850. In another embodiment, detection sensor 2810 may detect when the conductive flow 2840 has changed or been disrupted between the electrode 2830 and the tissue 2850 at the surgical site. When detection sensor 2810 detects that the electrode 2830 has disengaged from the tissue 2850, detection sensor 2810 sends a signal to controller 2080 to turn off RF generating system 2870 to the electrode 2830. In one example detection sensor 2810 senses operations parameters indicating that bipolar electrode 2830 has disengaged from tissue 2850 and a signal is sent to controller 2080. Controller 2080, in response, adjusts power settings from RF generating system 2870 to shut off power to bipolar electrode 2830 ending the electrical connection of electrode 2830 with body tissue 2850. In one example, the disengagement circuitry system 2820 is utilized prevent tissue damage or arcing.

Continuing with FIG. 28, electrode 2830 is in mechanical contact with stroke mechanism 2860 which provides a tolerance of mechanical movement of the electrode 2830 within a structure of a fixed position RF electrode 2800 to accommodate for contours in tissue 2850. In one example stroke mechanism 2860 provides for gap distance 2865 of 0.125 inches of movement of the electrode in compression within electrode support structure 2815. It should be understood that different gap distances 2865 may be used to increase or decrease tolerance of electrode 2380 with respect to tissue contours. This stroke mechanism 2860 allows some variation in engagement of electrode 2830 to tissue 2850 before detection sensor 2810 communicates a disengagement signal to the controller 2080. In another embodiment, such as fixed position RF electrode 100, the device may include disengagement circuits for both a first electrode 120 and second electrode 122.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A fixed position RF electrode for conducting surgical procedures, comprising:
   a main device body detachably connectable to an RF generating system;
   a first polarized conductor and a second oppositely polarized conductor;
   a bipolar electrical conduit passing through the main device body that passes RF energy from the RF generating system to the first polarized conductor and the second oppositely polarized conductor;
   a detachable bipolar electrode for contacting a surgically operative material, wherein said bipolar electrode comprises:
      an extension, wherein a first proximal end of the extension is detachably connected to the main device body, said extension encapsulating a portion of the first polarized conductor and a portion of the second polarized conductor;
      a first flexible electrode lead longitudinally connected at a first connection point to a distal end of the extension, said first flexible electrode lead in electrical communication with the first polarized conductor;
      a second flexible electrode lead longitudinally connected at a second connection point to the distal end of the extension, said second flexible electrode lead in electrical communication with the second polarized conductor;
      a first electrode portion electrically connected to a distal end of the first flexible electrode lead in electrical communication with the first polarized conductor; and
      a second electrode portion electrically connected to a distal end of the second flexible electrode lead in electrical communication with the second polarized conductor;
      a first liquid delivery conduit attached to the main device body and adapted to direct a first liquid to a region of the surgically operative material in electrical contact with the first electrode portion; and
      a second liquid delivery conduit attached to the main device body and adapted to direct a second liquid to a region of the surgically operative material in contact with the second electrode portion;
   wherein the first flexible electrode lead is adapted to bend laterally in all directions about the first connection point with the extension to adjust a position of the first electrode portion;
   wherein the second flexible electrode lead is adapted to bend laterally in all directions about the second connection point with the extension to adjust a position of the second electrode portion; and
   wherein the extension detaches from the main device body to remove the detachable bipolar electrode.

2. The fixed position RF electrode according to claim 1, wherein the first liquid from the first conduit and the second liquid from the second conduit increase a conductive pathway for electrical current to flow through the surgically operative material from the first electrode portion to the second electrode portion.

3. The fixed position RF electrode according to claim 2, wherein a position of the first flexible electrode lead angularly diverges from a position of the second flexible electrode lead to configure an angular spacing between the first and the second electrode portions and the extension; and
   wherein flexing the first and the second flexible electrode leads adjusts the angular spacing to improve visibility of a region of the surgically operative material.

4. The fixed position RF electrode according to claim 2, wherein the first flexible electrode lead and the second flexible electrode lead are comprised of a material with properties to permit bending of at least one of the first and second flexible electrode leads to adjust a position of at least one of the first and second electrode portions.

5. The fixed position RF electrode according to claim 2, wherein bending at least one of the first and second flexible electrode leads adjusts a position of the first electrode portion with respect to a position of the second electrode portion to modify a conductive pathway for electrical current to flow through the surgically operative material from the first electrode portion to the second electrode portion.

6. The fixed position RF electrode according to claim 5, wherein a width of the extension adjacent the first and the second flexible electrode leads is narrower than a maximum width at the first electrode portion and the second electrode portion.

7. The fixed position RF electrode according to claim 5, wherein a portion of at least one of the liquid delivery conduits comprises an external delivery conduit attached to an outer surface of the extension, said external delivery conduit further comprising an exit externally positioned to direct liquid to a region of the surgically operative material in electrical contact with at least one of the first and the second electrode portions.

8. The fixed position RF electrode according to claim 7, wherein the exit further comprises a micro perforation disposed within a cross-section of the exit and adapted to deliver liquid in the form of a sprayed mist.

9. The fixed position RF electrode according to claim 8, wherein the exit comprises a tubular shape and wherein an area of the sprayed mist forms a radial pattern.

10. The fixed position RF electrode according to claim 9, wherein the micro perforation is positioned at an angle which controls a spraying direction of the sprayed mist.

11. The fixed position RF electrode according to claim 10, wherein the first liquid delivery conduit terminates in the exit comprising the micro perforation adapted for delivery of the first liquid as a sprayed mist and wherein the second delivery conduit terminates in an opening adapted to deliver the second liquid as a flowing liquid.

12. The fixed position RF electrode according to claim 11, further comprising:
- a first liquid source providing the first liquid into the first liquid delivery conduit; and
- a second liquid source providing the second liquid into the second liquid delivery conduit;
- wherein at least one of the first and second liquids comprises a liquid from the group comprising saline, antibiotic, anti-coagulant and pain medicine liquids.

13. The fixed position RF electrode according to claim 10, further comprising:
- a combined mass of a group of materials comprising the bipolar electrode and
- a combined mass of a group of materials comprising main device body;
- wherein the combined mass of the group of materials comprising the bipolar electrode is substantially less than the combined mass of the group of materials comprising the main device body so that a center of gravity for the device is located in a handpiece disposed within main device body.

14. The fixed position RF electrode according to claim 5, wherein at least one of the electrode portions further comprises a protruding electrode feature adapted for applying focused RF energy to a region of the surgically operative material.

15. The fixed position RF electrode according to claim 14, wherein a shape of the protruding electrode feature is a pointed shape.

16. The fixed position RF electrode according to claim 5, wherein
the first flexible electrode lead further comprises:
- a first rigid electrode section extending from the extension at the first connection point;
- a first flexible electrode section in connection with the first rigid electrode section, the first flexible electrode section adapted to bend laterally in all directions to adjust the position of the first electrode portion disposed at the end of the first flexible electrode section; and wherein the second flexible electrode lead further comprises:
- a second rigid electrode section extending from the extension at the second connection point;
- a second flexible electrode section in connection with the second rigid electrode section, the second flexible electrode section adapted to bend laterally in all directions to adjust the position of the second electrode portion disposed at the end of the second flexible electrode section.

* * * * *